United States Patent
Khalil

(10) Patent No.: US 11,484,637 B2
(45) Date of Patent: Nov. 1, 2022

(54) AUTOIMMUNE MECHANICAL IMMUNOMODULATION

(71) Applicant: AMINA Sciences LLC, Houston, TX (US)

(72) Inventor: Nashwa A. Khalil, Houston, TX (US)

(73) Assignee: AMINA Sciences LLC, Houston, TX (US)

( * ) Notice: Subject to any disclaimer, the term of this patent is extended or adjusted under 35 U.S.C. 154(b) by 395 days.

(21) Appl. No.: 15/863,974

(22) Filed: Jan. 7, 2018

(65) Prior Publication Data

US 2018/0126060 A1    May 10, 2018

Related U.S. Application Data

(63) Continuation-in-part of application No. PCT/US2016/041396, filed on Jul. 7, 2016.

(Continued)

(51) Int. Cl.
*A61M 1/34*    (2006.01)
*A61M 1/36*    (2006.01)
*A61K 35/14*   (2015.01)

(52) U.S. Cl.
CPC ........... *A61M 1/3496* (2013.01); *A61K 35/14* (2013.01); *A61M 1/3455* (2013.01);
(Continued)

(58) Field of Classification Search
CPC .............. A61M 1/3496; A61M 1/3455; A61M 1/3693; A61M 2205/36;
(Continued)

(56) References Cited

U.S. PATENT DOCUMENTS 3,099,260 A *   7/1963   Birtwell ............... A61M 60/50
                                                    417/478
2001/0021817 A1*  9/2001  Brugger ............. A61M 1/3626
                                                    604/6.11
(Continued)

FOREIGN PATENT DOCUMENTS

WO    WO-2014147028 A1 *  9/2014   ......... A61B 5/02125

OTHER PUBLICATIONS

Haithcock, B.E., et al. "Hemodynamic Unloading of the Failing Left Ventricle Using an Arterial-to-Arterial Extracorporeal Flow Circuit," Ann. Thorac. Surg. 2004, 77(1), 158-63. doi:10.1016/s0003-4975(03)01199-8 (Year: 2001).*

(Continued)

*Primary Examiner* — Philip R Wiest
*Assistant Examiner* — Alessandro R Del Priore
(74) *Attorney, Agent, or Firm* — Umair A. Qadeer

(57) ABSTRACT

The present disclosure describes a novel therapeutic apheresis system and, more specifically, methods and an apparatus for performing therapeutic apheresis. The present disclosure provides highly efficient methods for therapeutic apheresis that modulate the immune system, thereby resulting in treatment of one or more underlying immunological disease processes. In some embodiments, the disclosed methods return at least a portion of blood from an extracorporeal circuit to a patient in pulsatile flow, where the portion of blood that is returned is augmented. In other embodiments, the disclosed methods and apparatus use the central arterial system to exchange volumes of plasma to immunomodulate disease processes.

19 Claims, 3 Drawing Sheets

Related U.S. Application Data

(60) Provisional application No. 62/445,714, filed on Jan. 12, 2017, provisional application No. 62/334,287, filed on May 10, 2016, provisional application No. 62/291,973, filed on Feb. 5, 2016, provisional application No. 62/254,005, filed on Nov. 11, 2015, provisional application No. 62/189,678, filed on Jul. 7, 2015.

(52) U.S. Cl.
CPC ... *A61M 1/3693* (2013.01); *A61M 2202/0478* (2013.01); *A61M 2205/054* (2013.01); *A61M 2205/10* (2013.01); *A61M 2205/127* (2013.01); *A61M 2205/3331* (2013.01); *A61M 2205/3344* (2013.01); *A61M 2205/3368* (2013.01); *A61M 2205/36* (2013.01); *A61M 2205/366* (2013.01); *A61M 2206/10* (2013.01); *A61M 2230/04* (2013.01)

(58) Field of Classification Search
CPC .... A61M 2205/3331; A61M 2205/366; A61M 2205/127; A61M 2202/0478; A61M 2206/10; A61M 2230/04; A61M 2205/3344; A61M 2205/3368; A61M 2205/054; A61M 2205/10; A61M 1/3601; A61M 2021/0061; A61K 35/14
See application file for complete search history.

(56) References Cited

U.S. PATENT DOCUMENTS

| | | | | |
|---|---|---|---|---|
| 2004/0015042 | A1* | 1/2004 | Vincent | A61M 60/40 600/17 |
| 2007/0215545 | A1* | 9/2007 | Bissler | A61M 1/1613 210/646 |
| 2009/0099498 | A1* | 4/2009 | Demers | A61M 60/40 604/6.09 |
| 2011/0257577 | A1* | 10/2011 | Lane | A61M 1/3655 604/6.11 |

OTHER PUBLICATIONS

Mavroudis, C. "To Pulse or Not To Pulse," Ann. Thorac. Surg. 1978, 25(3), 259-71. doi:10.1016/s0003-4975(10)3539-4 (Year: 1978).*

Cordero-Reyes, A.M., et al. "The Role of B-Cells in Heart Failure," Methodist Debakey Cardiovasc. J. 2013, 9(1), 15-19. doi:10.14797/mdcj-9-1-15.

Estep, J.D., et al. "Percutaneous Placement of an Intra-Aortic Balloon Pump in the Left Axillary/Subclavian Position Provides Safe, Ambulatory Long-Term Support as Bridge to Heart Transplantation," JACC Heart Fail. 2013, 1(5), 382-88. doi:10.1016/j.jchf.2013.06.002.

Haithcock, B.E., et al. "Hemodynamic Unloading of the Failing Left Ventricle Using an Arterial-to-Arterial Extracorporeal Flow Circuit," Ann. Thorac. Surg. 2004, 77(1), 158-63. doi:10.1016/s0003-4975(03)01199-8.

Hiepe, F., et al. "Autoantikörper und die Zellen, die sie machen [Autoantibodies and Antibody-Secreting Cells]," Z Rheumatol. 2005, 64(6), 389-95. doi:10.1007/s00393-005-0767-8.

Hiepe, F., et al. "Long-Lived Autoreactive Plasma Cells Drive Persistent Autoimmune Inflammation," Nat. Rev. Rheumatol. 2011, 7(3), 170-78. doi:10.1038/nrrheum.2011.1.

Klotz, L., et al. "Cardiac Lymphatics are Heterogeneous in Origin and Respond to Injury," Nature, 2015, 522(7554), 62-67. doi:10.1038/nature14483.

Leyendeckers, H., et al. "Correlation Analysis Between Frequencies of Circulating Antigen-Specific IgG-Bearing Memory B Cells and Serum Titers of Antigen-Specific IgG," Eur. J. Immunol. 1999, 29(4), 1406-17. doi:10.1002/(SICI)1521-4141(199904)29:04<1406::AID-IMMU1406>3.0.CO;2-P.

Maruyama, M., et al. "Memory B-Cell Persistence Is Independent of Persisting Immunizing Antigen," Nature, 2000, 407(6804), 636-42. doi:10.1038/35036600 [published correction appears in Nature, 2001, 409(6818), 382].

Mavroudis, C. "To Pulse or Not To Pulse," Ann. Thorac. Surg. 1978, 25(3), 259-71. doi:10.1016/s0003-4975(10)63539-4.

Mei, H.E., et al. "A Unique Population of IgG-Expressing Plasma Cells Lacking CD19 Is Enriched in Human Bone Marrow," Blood, 2015, 125(11), 1739-48. doi:10.1182/blood-2014-02-555169.

Ochsenbein, A.F., et al. "Protective Long-Term Antibody Memory by Antigen-Driven and T Help-Dependent Differentiation of Long-Lived Memory B Cells to Short-Lived Plasma Cells Independent of Secondary Lymphoid Organs," Proc Nat'l Acad. Sci. U S A. 2000, 97(24), 13263-68. doi:10.1073/pnas.230417497.

Petretta, M., et al. "Circulating Levels of Cytokines and Their Site of Production in Patients with Mild to Severe Chronic Heart Failure," Am. Heart J. 2000, 140(6), E28. doi:10.1067/mhj.2000.110935.

Scallan, J., et al. Capillary Fluid Exchange: Regulation, Functions, and Pathology, San Rafael, CA: Morgan & Claypool Life Sciences, 2010.

"Techniques in ExtraCorporeal Circulation," J. Extra Corpor. Technol. 2005, 37(1), 79.

Torre-Amione, G., et al. "Therapeutic Plasma Exchange a Potential Strategy for Patients with Advanced Heart Failure," J. Clin. Apher. 2010, 25(6), 323-30. doi:10.1002/jca.20264.

* cited by examiner

AUTOIMMUNE MECHANICAL IMMUNOMODULATION

CROSS-REFERENCE TO RELATED APPLICATIONS

This application is a continuation-in-part of PCT Patent Application No. PCT/US2016/041396, filed on Jul. 7, 2016, which claims the benefit of and priority to U.S. Provisional Patent Application Ser. No. 62/189,678, filed on Jul. 7, 2015, U.S. Provisional Patent Application Ser. No. 62/254,005, filed on Nov. 11, 2015, U.S. Provisional Patent Application Ser. No. 62/291,973, filed on Feb. 5, 2016, and U.S. Provisional Patent Application Ser. No. 62/334,287, filed on May 10, 2016; and this application also claims the benefit of and priority to U.S. Provisional Patent Application Ser. No. 62/445,714, filed on Jan. 12, 2017; the disclosures of which are incorporated herein in their entireties by reference.

BACKGROUND

Field of the Invention

The present disclosure relates to therapeutic apheresis.

Description of the Related Art

The present disclosure relates to therapeutic apheresis. Therapeutic apheresis is the process of transiently removing blood from the body, separating it into various components (e.g., cells, plasma, proteins, antibodies, antigen-antibody complexes, lipids, etc.), removing those components that contribute to disease, and then returning the remaining blood with possible addition of a blood component to the body. Apheresis medicine is the discipline of medicine, engineering, and science that includes the care and management of patients involved in extracorporeal blood separation interventions used in the treatment of diseases. Although a variety of specialists such as hematologists, neurologists, nephrologists see the evidence and benefits of therapeutic apheresis in their everyday work, the progress of apheresis medicine as a medical specialty has been generally slow. There is a lack of in depth understanding of basic mechanisms of apheresis and optimal ways of applying apheresis to the improvement of underlying conditions.

As described above, apheresis is a process in which blood of a donor or patient is passed through an apparatus that separates out one or more components and returns the remaining blood to the donor or patient. Apheresis is, therefore, an extracorporeal therapy. A patient is typically given 5-15 therapeutic apheresis sessions based on a rough estimate from historical patient data for repressing symptomatic disease. A patient may be treated this way for years because the actual underlying immune disease process affecting the patient has not been effectively treated.

Traditional methods of therapeutic apheresis are performed by plasma exchange using peripheral vasculature of the venous pathway. Traditional therapeutic apheresis is performed by utilizing peripheral venous catheter lines to exchange approximately three liters of plasma with approximately three liters of a replacement fluid. The replacement fluid is usually albumin, one or more blood products, or other acceptable forms of volume expanders such as hydroxyethyl starch.

Under traditional methods of therapeutic apheresis, only immune factors and entities that are part of the plasma floating in the bloodstream at the time of treatment are removed from the body. Significantly, in traditional therapeutic apheresis there is no augmentation of the plasma contents within the blood stream or the hemodynamics of blood flow before or during treatment. Thus, the concentrations of immune factors and other entities within the secondary lymphoid system attached to the blood vascular system in the body remain unchanged and such immune factors and other entities within the secondary lymphoid system are not removed. Therefore, the signaling pathways of the patient's immunological disease process that exist in the secondary lymphoid system are intact and do not change. Hence, the patient's underlying immunological disease process remains constant.

There have been many attempts to improve the efficacy of therapeutic apheresis, but none to date effectively change the concentration and migration of immune factors and their related signaling pathways. The concentration and migration of immune factors relative to other immune factors in the tissue, vascular, and lymphatic systems of the body affects functions of the overall immune system. Conventional therapeutic apheresis offers, at best, only symptomatic relief without treatment of underlying immunological disease process.

There remains a significant need for systems and methods of therapeutic apheresis that change the concentration and migration of immune factors relative to other immune factors in the tissue, vascular, and lymphatic systems of the body.

SUMMARY

The present disclosure describes a novel therapeutic apheresis system and, more specifically, methods and an apparatus for performing therapeutic apheresis. The present disclosure provides highly efficient methods for therapeutic apheresis that modulate the immune system, thereby resulting in treatment of one or more underlying immunological disease processes.

In some embodiments, the method of therapeutic apheresis returns at least a portion of blood from an extracorporeal circuit to a patient in pulsatile flow, wherein the portion of blood that is returned is augmented. In other embodiments, the methods and systems of the present disclosure use the central arterial system to exchange volumes of plasma to immunomodulate disease processes. The present disclosure is based in part on combining concepts of intermittent flow and continuous flow therapeutic apheresis with established cardiovascular concepts. The disclosed methods of therapeutic apheresis decrease the amount of time spent by patients in therapeutic apheresis sessions. The disclosed methods of therapeutic apheresis also decrease patients' dependence on immunological drugs that may have detrimental adverse effects. The term "patient" is broadly defined herein to include both humans and animals.

All disease states involving immune processes currently using traditional therapeutic apheresis methods and immunological drugs to depress parts or all of the immune system may benefit from the therapeutic apheresis system and methods described herein. In addition, other immunological disease processes that improve with immunomodulation, such as organ transplant (including immunosuppression/rejection and induction/desensitization), established infections, allergies, needs of vaccine work such as inverse vaccine, and cancer states, may benefit from use of the therapeutic apheresis system and methods described herein.

Due to improvement in efficacy of this form of apheresis, it may be used in pathology states in which avoiding immune complex injury (e.g., inflammation) and/or preventing the build-up of immune factors/inflammation is beneficial. The disclosed methods of therapeutic apheresis may prevent the resultant damage caused by such states; for example, in cardiac conditions in which immune pathology occurs.

DETAILED DESCRIPTION OF THE ILLUSTRATED EMBODIMENTS

Figure 1:
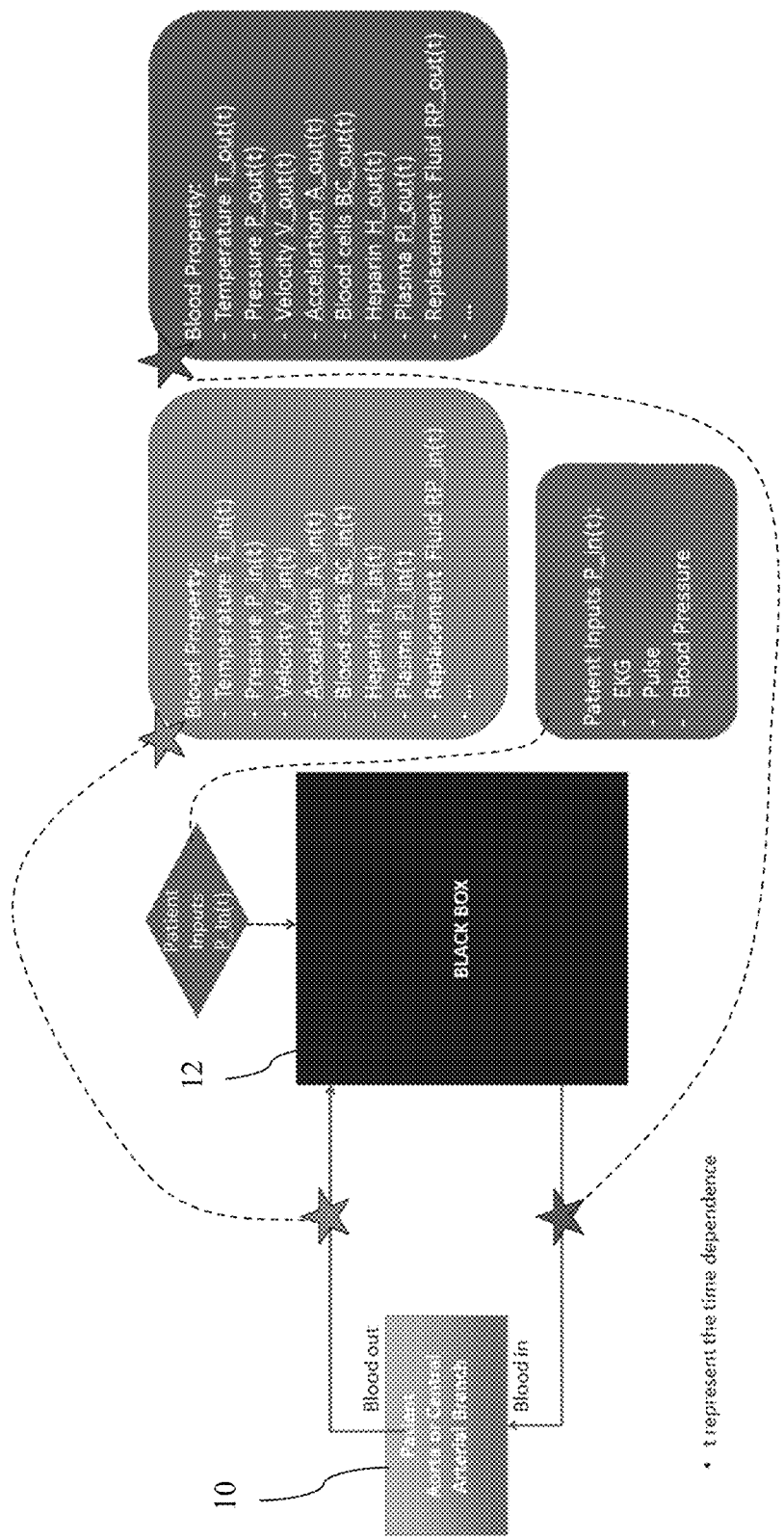
FIG. 1 is a schematic diagram of one embodiment of the present disclosure.

The present disclosure describes a novel therapeutic apheresis system and, more specifically, methods and an apparatus for performing therapeutic apheresis. The present disclosure provides highly efficient methods for therapeutic apheresis that modulate the immune system, thereby resulting in treatment of one or more underlying immunological disease processes.

As used herein, the term "blood" refers to whole blood or any substituent component of whole blood.

In some embodiments, the method of therapeutic apheresis returns at least a portion of blood from an extracorporeal circuit to a patient in augmented pulsatile flow. In other embodiments, the methods and systems of the present disclosure use the central arterial system to exchange volumes of plasma to immunomodulate disease processes. The present disclosure is based in part on combining concepts of intermittent flow and continuous flow therapeutic apheresis with established cardiovascular concepts. The disclosed methods of therapeutic apheresis decrease the amount of time spent by patients in therapeutic apheresis sessions, not only during initial treatment processes but throughout the course of the patients' lives. The disclosed methods of therapeutic apheresis also decrease patients' dependence on immunological drugs that may have detrimental adverse effects. The term "patient" is broadly defined herein to include both humans and animals.

All disease states involving immune processes currently using traditional therapeutic apheresis methods and immunological drugs to depress parts or all of the immune system may benefit from the therapeutic apheresis system and methods described herein. In addition, other immunological disease processes that improve with immunomodulation, such as organ transplant (including immunosuppression/rejection and induction/desensitization), established infections, allergies, needs of vaccine work such as inverse vaccine, and cancer states, may benefit from use of the therapeutic apheresis system and methods described herein.

Due to improvement in efficacy of this form of apheresis, it may be used in pathology states in which avoiding immune complex injury (e.g., inflammation) and/or preventing the build-up of immune factors/inflammation is beneficial. The disclosed methods of therapeutic apheresis may prevent the resultant damage caused by such states; for example, in cardiac conditions in which immune pathology occurs.

The disclosed novel therapeutic apheresis system and methods allows changes that disrupt survival signaling pathways of disease-causing underlying immune processes.

Immunological disease processes are complicated by two phenomena related to immune factors. Immune factors, such as antibodies, between the intra- and extravascular space directly or indirectly damage tissues that perform essential functions. Increases and changes in migrations of immune factors or other entities in the extravascular space also cause perpetual signal production to make ever increasing levels of immune factors that results in increased immune complex reactions and tissue damage.

The disclosed system and methods increase the velocity and pulsatility of arterial perfusion. Simultaneously, immune factors are removed from the plasma of arterial blood, and blood that has been plasma-depleted, including immune factors, is returned to the patient upstream in the central arterial system. This blood is returned at augmented velocity and pulse to the capillary level/lymphatic system via the arterial tree. The mechanism for transvascular flux of proteins, a shift of plasma proteins, is due to a decrease in plasma protein concentration that causes increase in lymph flow, which is greater than transvascular protein permeability. As a result, there is greater migration of immune factors from extravascular space into the intravascular space; and, once in the intravascular space, they can be removed via the continuous plasma exchange process disclosed herein.

Overall, the system and methods disclosed herein allow the immune regulation pathways, particularly humoral, to be "reset" by mechanically augmenting hemodynamics of arterial flow while simultaneously removing immune factors from the arterial flow. When the flow and concentration of immune factors in the secondary lymphoid system that is responsible for signaling pathways of a patient's current disease process are removed due to this process, immunity is changed. The body's native modalities of migration pathways return to standard immune regulation in the extravascular.

The disclosed system and methods focus on the secondary lymphoid system, which is attached to the arterial vascular system. Input of immune factors and cells into germinal centers of the secondary lymphoid system occurs from blood traveling via the vascular system. It is well understood how and why immunological pathways may malfunction and result in immune disease. Immunological systems function via the communication of specific cells and factors to effect immunity. Migratory patterns, or the lack thereof, of cells and immune factors are affected by the hemodynamics of blood traveling in the vascular system.

Arterial perfusion is responsible for movement of immune factors between intra- and extravascular spaces via the lymphatic system. The disclosed therapeutic apheresis system and methods change the gradients of immune factors and other entities downstream at the capillary level between intra- and extravascular by augmenting arterial perfusion. The native modalities of migration pathways that affect immune regulation are intact and there are not severe adverse effects as seen with many drugs that are currently used to treat immunological disease processes.

In general, the present disclosure is directed to a system and methods of using an extracorporeal circuit configured to intake arterial blood from a patient, performing apheresis on the blood to remove one or more components from the blood, and returning the blood in an augmented or increased velocity of pulsatile flow that changes the pulse amplitude in at least a portion of the blood from the extracorporeal circuit. This creates an overall change in the velocity of total blood flow that occurs at during systole. As used herein, "pulsatile flow" refers to flow with periodic variations in velocity (e.g., varying speeds of operation of a pump). The change in the energy of the blood traveling through the arterial system to the end of the arterial tree changes the flow of immune factors and other entities within the secondary lymphatic system. This allows for changes in migrations and unique concentrations of immune factors and other entities from the secondary lymphatic system to enter intravascular space for removal as plasma is exchanged via arterial pathways.

In some embodiments, the disclosed methods create an immunomodulatory effect on a patient's immune system. The term "immunomodulation" (and its derivatives) is broadly defined herein to encompass any adjustment of the immune response to a desired level, as well as all therapeutic interventions aimed at modifying the immune system (e.g., by inducing, enhancing, suppressing, and/or augmenting a patient's immune system). In some embodiments, the disclosed therapeutic apheresis system and methods may be combined with one or more disease modifying treatments, such as immunosuppressive drugs or other therapeutic agents, suitable for use or treatment of the patient.

The pulsatile component of arterial blood flow results from intermittent ventricular ejections. Blood flow in the microcirculation continues until a specific critical closing pressure in the pre-capillaries is reached; pulsatility prolongs that period of capillary opening and blood flow. Lymphatic flow is greatly reduced when blood flow is de-pulsed. Pulsatility affects capillary blood flow and diameter irrespective of total blood flow and mean pressure. Pulsatility affects differential pore distribution at the capillary level. It has also been suggested that pulsatility is responsible for fluid balance. Hence, pulse is not only extremely significant directly to lymphatic flow but the effect of the energy from pulsatile flow on capillary and tissue exchanges influences migration between the intra- and extravascular.

The disclosed therapeutic apheresis system and methods increase the velocity in the arterial system via increasing the energy augmenting the pressure wave of blood transmission throughout the arterial system. The change or increase in blood flow velocity in at least a portion of the blood with simultaneous plasma exchange and transvascular flux of proteins throughout the arterial system connected to the secondary lymphatic system immunomodulates underlying immune disease processes. In some embodiments, optimization of the effects of the pulse wave incorporates considerations of pulse wave reflections when augmenting pulsatility. This is achieved by editing the pulse wave transmission of blood flow ejected into the central arterial system. The overlap is influenced by the relationships between transit time of pressure waves from the aorta to reflecting sites and back, and duration of left ventricular ejection (heart rate).

Changes in aortic geometry (tapering), via local arterial branching and lumen narrowing, creates an impedance mismatch causing partial reflections ("echo") of forward progressing incident pressure waves, i.e., a reflected wave, travelling back to the central aorta, and leading to changes in the amplitude of systolic and pulse pressure along the arterial tree. Forward and reflected pressure waves are overlapping and are reflected in the measured pressure wave. The final amplitude and shape of the measured pulse pressure wave is determined by the phase relationship (the timing) between the component waves, i.e., the overlap between the two waves which depends on the site of pressure recording in the arterial tree. In central arteries, the forward and reflected waves are not in phase, and the shape and amplitude of pressure wave depends on the overlap between the forward wave and the reflected wave. The overlap between forward and reflected pressure waves depends on the PWV (an assessment of stiffness of an artery as a hollow structure) and traveling distance of pressure waves to reflection sites and the left ventricular ejection time duration as a determinant of the overlap possibility.

In some embodiments, the extracorporeal circuit may be operably connected to the circulatory system of a patient. For central arterial access to the aorta, a catheter may be inserted into the patient via the subclavian artery. Alternatively, a catheter may be inserted into the femoral artery, which is a pathway to the aorta. Arterial access for catheters may be radiologically guided and may follow standard arterial catheter access for vascular procedures. Similarly, a catheter may be inserted into one or more major anatomical branches of the central arterial system instead of the aorta, depending on the pathological state needing treatment. Different return blood flow velocities may be created or produced in the different major anatomical branches throughout the central arterial system, depending on the pathological states, such as neurological and/or orthopedic conditions, benefitting from this form of apheresis.

In some embodiments, the disclosed extracorporeal circuit may include an automated blood cell separator. The automated blood cell separator may be used to ensure fluid balance and maintain a normal plasma volume. Continuous flow centrifugation or intermittent flow centrifugation methods may be employed for apheresis. In some embodiments, the extracorporeal circuit includes an apheresis centrifuge. The centrifuge may be sized to handle processing of amounts of blood at higher volumes and faster flow as part of the plasma exchange required to support blood flow where pulse is being augmented.

In some embodiments, the pulsatile flow from the extracorporeal circuit is provided by the force from one or more pumps. In other embodiments, the pulsatile flow from the extracorporeal circuit is provided through electrical stimuli to the heart in order to augment the pulse wave from the heart. In such embodiments, blood may be returned to the patient at a generally constant rate while still having the desired pulsatile flow properties.

In some embodiments, the disclosed extracorporeal circuit may include one or more pumps. In general, the one or more pumps are capable of returning to a patient at least a portion of the blood from an extracorporeal circuit. In certain embodiments, the pump also may be capable of returning the portion of the blood in pulsatile flow. Suitable pumps include positive displacement pumps, roller pumps, ventricular pumps, piston pumps, kinetic pumps, centrifugal pumps, forced vortex pumps, and magnetic pumps. In some embodiments, the one or more pumps may be disposed within an indwelling catheter. In some embodiments, the one or more pumps may have an output that approximates systolic flow output of the left ventricle. In some embodiments, the one or more pumps may have a variable displacement, timing, and fill/eject ratio control. The one or more pumps may be configured to operate within a variable range, such that blood may be pumped at a rate from approximately 0.1 liters/minute to as high as 1.5 liters/minute, 0.5 liters/minute to as high as 1.0 liter/minute, and 0.3 liters/minute to as high as 0.6 liters/minute. In some embodiments, one or more of the pumps can be extracorporeal or located at or near an end of an indwelling catheter, wherein the indwelling catheter is placed in the aorta or central arterial branches of the patient and is configured to deliver axial flow.

In some embodiments, the one or more pumps may be operatively connected to a controller. The controller may be configured to produce one or more signals to the pump(s), and each pump may be configured to act in accordance with information contained in each signal it receives from the controller. The controller controls the pump and allows for pulsatile flow of the portion of the blood returned to the patient from the extracorporeal circuit. In some embodiments, the controller modulates the volumetric flow rate of the pump to coincide with the onset of ventricular systole. The controller also may receive inputs about the native electrocardiogram of the patient or the paced rhythm. The controller may then provide information to the one or more pumps to effectuate return of blood to the patient via the arterial system. The control may also be configured to sense various pressures of patient (e.g., blood pressure) and decrease or increase the pump speed to compensate as necessary. The control may also be configured to sense other physiologic parameters, such as bioimpedence, body motion and/or cardiac performance parameters, to adjust pump speed to optimize flow of blood to the patient. The controller also may be operatively connected to other components of the disclosed system. For example, the controller may be configured to produce and/or receive signals from an automated blood cell separator, temperature sensors, pressure sensors, an air embolus sensor, pulse sensor (e.g., EKG) and/or a heat exchanger. Standard power delivery devices may be used in conjunction with the controller delivering proper wattage to allow operation of the disclosed system.

In some embodiments, one or more of the signals from the controller may cause one or more of the pumps to pulsate blood flow to the patient. More particularly, one or more of the pumps may have the capacity to pump pulsatile blood flow to the patient, such that the pulsatile blood flow returns to the patient in axial flow. The controller may vary pump speed either in synchronization with the heart rhythm or a paced rhythm, or out of synchronization with the heart rhythm. In other words, the pulsation may mimic the rhythm of the patient's heart. Attempting to sync the flow of blood to the patient with the patient's heart rate or a target heart rate is believed to improve the effectiveness of the treatment. The synced flow of blood is also returning with an augmented velocity using pumps to affect the amplitude of waves returning. By way of explanation and not limitation, mathematical and physical models have shown that, at the same mean pressure, pulsatile blood flow has approximately 2.4 times the energy content of non-pulsatile flow, thereby dissipating significantly more energy through the tissue. Pulsation directly impacts blood flow within the lymphatic system, and energy from pulsatile flow on capillary and tissue exchanges influences what occurs with substances from tissues into the lymphatic system. In some embodiments, the controller is configured such that the initiation of the ejection from the pump may occur at systole, less than or about 75 milliseconds after onset of systole as measured by EKG trace. The controller also may include a programmed delay up to 100 milliseconds to allow for tuning of the ejection start to the EKG signal being delivered. The pressure ranges of operation of the system have been identified are related to baseline pressures of the patient and the algorithm. The baseline pressures of a patient can be varied dependent on patient (human or animal) and their disease states. The algorithm used can be subject to modification based on patient needs or plasma exchange properties based on, for example, the patient's physiological profile and/or disease.

In some embodiments, the system comprises one or more EKG sensors and/or one or more pressure sensors. The EKG sensors detect EKG signal and are connected to a controller in a way that allows sending of the EKG signals to the controller. This allows the controller to detect different timepoints in the cardiac cycle such as QRS. Pressures sensors that are able to detect heart and aortic pressures sending signal to controller may also be connected to the controller.

In some embodiments, the controller is configured to receive information about temperature of the blood and to control a heat exchanger. The heat exchanger may be used to adjust the temperature of the blood returned to the patient. The controller, in conjunction with a heat exchanger, may vary returned blood temperature either in synchronization with the current body, normal range temperature, or increased temperature. The heat exchanger may be used to ensure that the temperature of blood being returned to the patient is at an appropriate or acceptable temperature to reduce afterload resistance.

In some embodiments, the controller also includes a pulse generator configured to produce one or pacing signals to the heart (e.g., electrical stimuli) to augment the pulse wave of the blood returned to the patient. In such embodiments, the controller may be operably connected to one or more leads placed on or in the heart and located distally at the end of an indwelling catheter. The controller receives sensing signals from leads (e.g., EKG events), and the pulse generator within the controller is configured to produce one or more pacing signals to the leads based on the sensing signals. In such configurations, augmented pulsatile flow of the returning portion of the blood from extracorporeal circuit to the patient is affected without a mechanical pump pulsing flow while still stimulating lymphatic circulation in the patient's secondary lymphoid system.

In some embodiments, velocity amplitudes of the blood flow returned to the patient may be modified (e.g., increasing and/or decreasing) from the baseline, while maintaining, increasing, or decreasing the baseline pulse frequency. In this way, different velocities in blood flow return may be created in order to effect changes in migration of components that affect immunomodulation.

The disclosed system may also include one or more pressure sensors, heat sensors, pulse sensors (e.g., electrocardiography (EKG) machine), or any combination thereof. One or more heat exchangers may be used. Suitable heat exchangers may be able to heat at least a portion of the blood up to 5 degrees Fahrenheit above the normal body temperature range. In certain embodiments, a reservoir system may be used to facilitate processing of the blood and resultant components with respect to plasma exchange. Source selection may switch between fill and eject sequences. In addition, a controller and/or monitor board may receive one or more patient inputs, such as blood properties, and track and/or display blood properties of the portion of the blood returned to the patient.

In some embodiments, the controller is configured, through an algorithm, to calculate the desired properties of the blood being returned to the patient. The purpose of the algorithm is to evaluate the augmentation, changes, or modifications of blood properties desired. The algorithm may be subject to modification based on patient needs or plasma exchange properties based on, for example, the patient's physiological profile and/or disease state. Plasma exchange properties relate to blood properties with regards to pulsatility, velocity of flow, and/or temperature.

In some embodiments, the algorithm may identify the onset of systole to enable the syncopation of a mechanical system with the pulse wave in the arterial system. This will include a lead time for proper response to onset of systole events. The algorithm may detect timepoints in the QRS complex, in particular the Q-wave peak, to provide a trigger after an adjustable delay. The real time EKG signal being provided to the algorithm would at a minimum be derived from a 3-lead collection. In response, the mechanical system may respond to triggers with the task of delivering a pressure pulse that augments the pulse wave including amplifying it by increasing the blood flow velocity. The mechanical system may operate with variable displacement (stroke volume), timing (heart rate), and fill/eject ratio control (systolic period). It may allow for time triggered execution of phase change and/or for immediate transition from fill to eject.

In some embodiments, heart failure patients with a decreased ejection fraction, will benefit from increased blood flow velocity that improves perfusion to the capillaries for exchange. This is achieved in the disclosed system by increasing the energy of the mass traveling down the aorta. The increased energy may be created via pump to produce changes in augmented pulsatile properties of stroke volume ejected as part of the system. These changes in pulsed flow of blood allows for perfusion to more tissue. Specifically, in patients with a decreased ejection fraction, in such embodiments the pumps can increase flow up to 2 liters per minute during treatment. This increase in flow in these patients accommodates the decreased ejection fraction to facilitate the effect on immune factors and other entities in the secondary lymphatic system. Simultaneously, the pump affects the amplitudes of the flow (pulse) while plasma is exchanged resulting in a durable effect on migrations from the extravascular.

Tubing or catheters used in the disclosed system to move blood or other fluids may be made of any suitable biocompatible or biomaterial. For example, plastic materials, such as those having the requisite strength and bio-compatibility characteristics and permitting the function of directional flow, may be used. Rigid biomaterials or flexible biomaterials may alternatively or additionally be utilized for the construction. Examples of suitable tubing materials include those commonly used for extracorporeal circulation, such as apheresis, hemodialysis, cardiopulmonary bypass, and extracorporeal membrane oxygenation (ECMO).

In some embodiments, the disclosed system uses tubing materials having low dielectric constant, low coefficient of friction, non-reactivity, or combinations thereof. Examples of suitable tubing materials include polytetrafluoroethylene (PTFE) and perfluoroalkoxy (PFA).

As noted above, the disclosed system may include an extracorporeal circuit for apheresis. In some embodiments, such apheresis includes adding a replacement fluid to the blood. The replacement fluid may be fresh frozen plasma (FFP) and/or a predetermined percentage of albumin and/or saline solution. Heparin and/or saline may be added to the replacement fluid depending upon patient needs. Saline and/or heparin may be added to the procedure before and/or during the procedure. However, saline and heparin are not required to be added to the system, or can be added via peripheral venous vascular system. In some embodiments, saline may be added in amounts that are consistent with the industry standard of care and used for hydration, as understood by those skilled in the art. In some embodiments, patients are given heparin following standard anticoagulation given during vascular and plasma exchange procedures. Although hypocalcaemia due to citrate-based anticoagulants is a common minor adverse event of therapeutic apheresis, sodium citrate is widely accepted because healthy donors are able to handle it better. Heparin is better for sicker populations. Using heparin will maintain a static state of calcium ion activity. Citrate based anticoagulants bind with calcium ions. Decrease in calcium ions may cause increase in cardiac adverse events such as arrhythmias. For this reason, heparin has been safely used in cardiac applications for many years. Heparin is standard for the care for patients undergoing vascular procedures.

In some embodiments, the length of time and amount of volume exchanged per treatment will be dependent on the severity and pathology of immunological process needed to affect immunological niches. This is so that the self-perpetuating cycles of these immunological processes in the niches are broken before being able to build up more of the immunological factors. Using the disclosed system, a decrease of replacement fluid using the above described controls of processing flow of blood will decrease needed replacement fluid. This allows flexibility in the amount of plasma exchange that needs to occur per treatment. In traditional therapeutic apheresis, the amount of plasma exchange is limited due to the required minimal amount of clotting factors and albumin (or volume expander) in plasma. In the disclosed system, the amount of replacement fluid exchanged for plasma is decreased because the amount of change in migrations and concentrations of immune factors and other entities that occurs is more effective in treating underlying disease processes. Hence, the disclosed system allows for higher exchange rates of needed portions of blood without increasing the required amount of replacement fluid. In some cases, a longer period of time per treatment may be needed due to the type and severity of the disease process. In such cases, even though plasma exchange may be efficient, increased volume plasma exchanged may require fresh frozen plasma. This procedure will be able to replace more than the standard 1-1.5 liter volume, as needed.

In some embodiments, the replacement fluid in the blood returning to the patient may include one or more therapeutic agents such as one or more drugs, immune factors, cells, nanoparticles, and/or vectors. Replacement fluids that include therapeutic agents allow for more effective delivery of such therapeutic agents. Replacement fluids including therapeutic agents may be exchanged as a full volume exchange or an exchange in any amount less than full volume. The length of time, amount of volume exchanged, ratio of exchange, and concentrations of factors in constituents/replacement fluid returned per treatment in the disclosed therapeutic apheresis system may be dependent on the severity and pathology of disease process and the particular therapeutic agent, among other factors.

Figure 2:
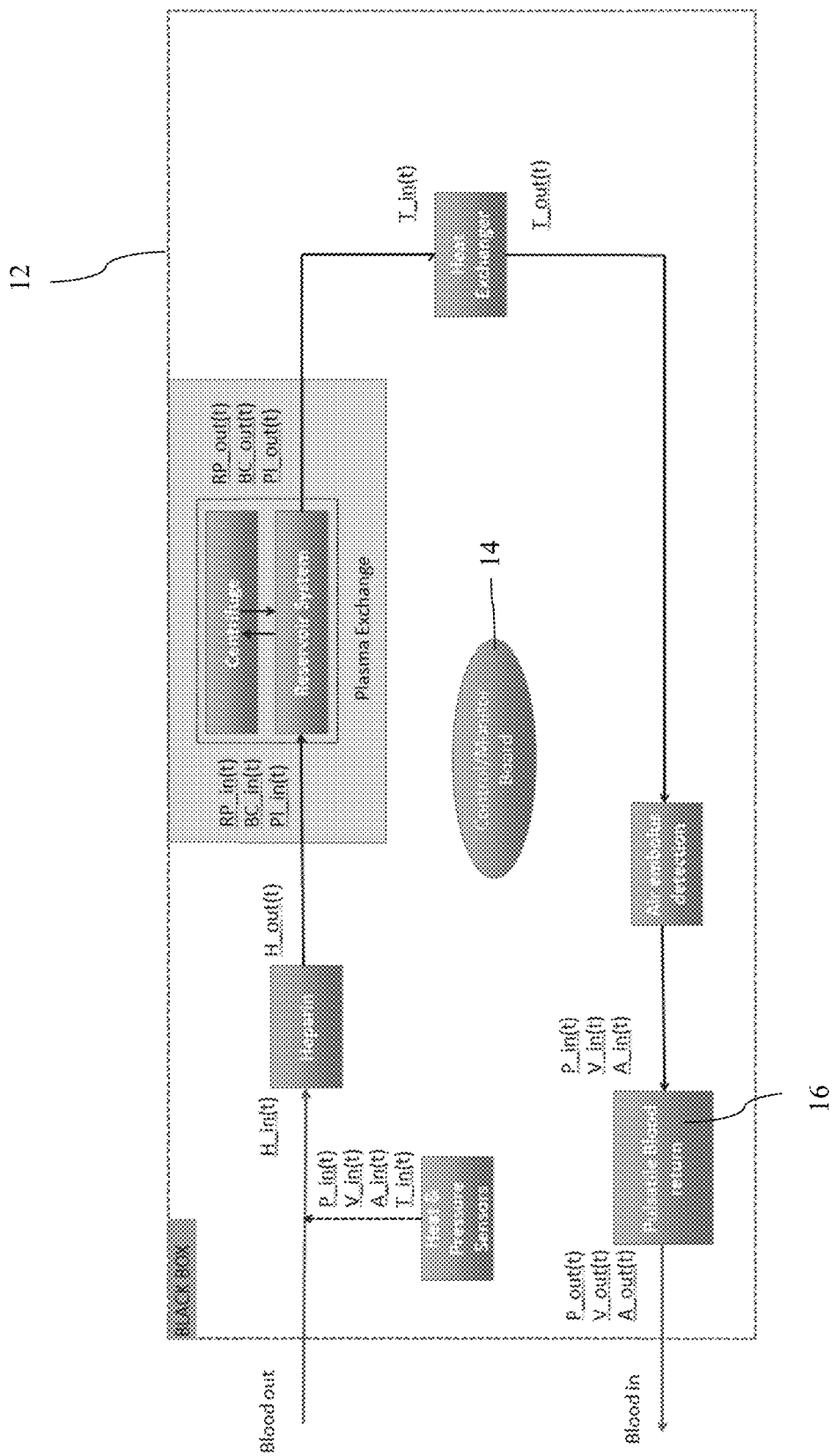
FIG. 2 is a schematic diagram showing additional details of a portion of the schematic diagram of FIG. 1.
Figure 3:
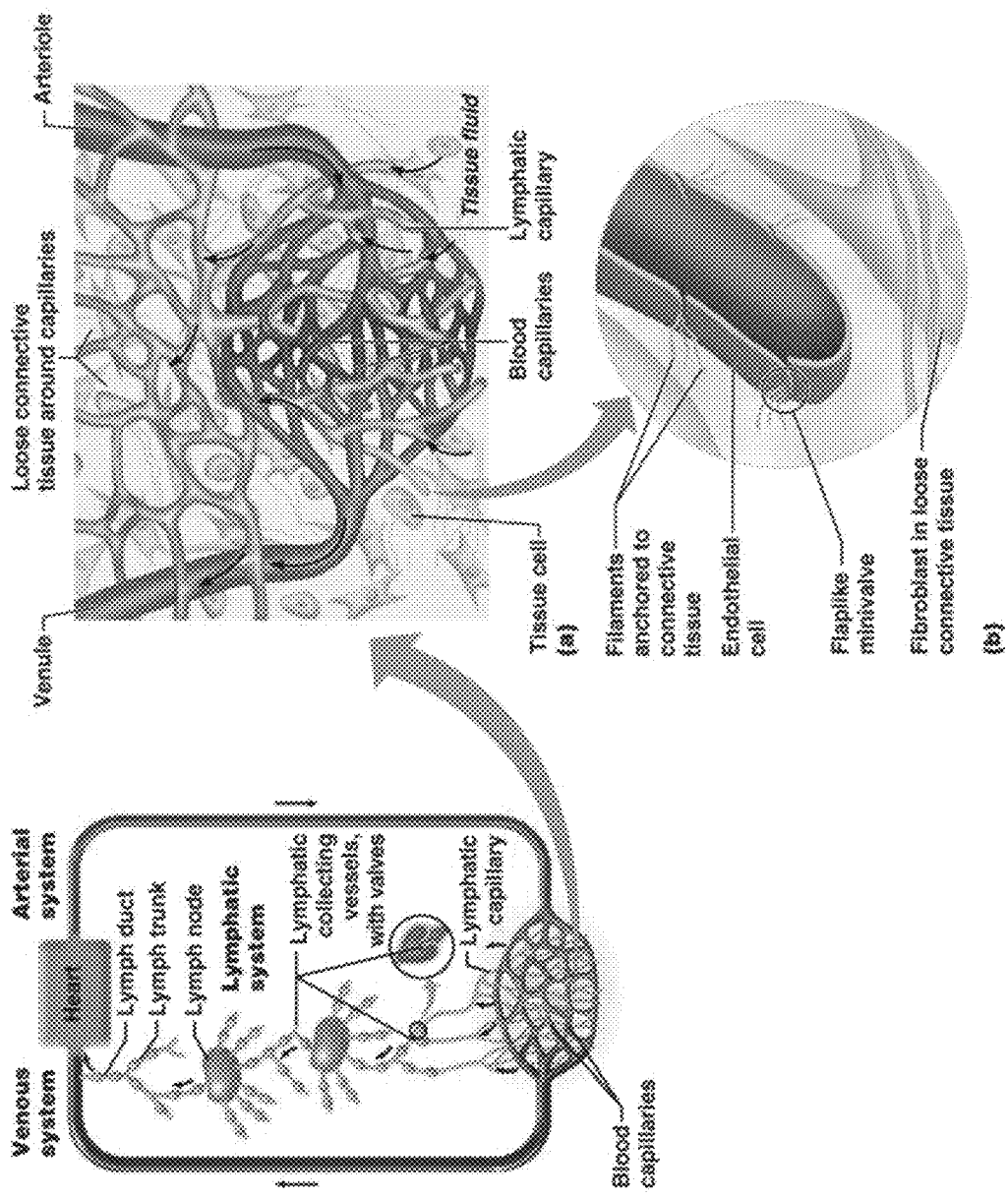
FIG. 3 is a schematic diagram showing portions of the human venous and arterial systems.

FIGS. 1 and 2 illustrate an embodiment of the present disclosure. In particular, blood is received from the aorta or central arterial branches of the patient, generally designated 10, and transmitted to and/or through an extracorporeal circuit, generally designated 12. Certain properties of the blood, such as temperature (T), pressure (P), velocity (V), acceleration (A), number and/or type of certain blood cells (BC), heparin (H) levels, plasma (Pl) levels and/or the like, is measured or analyzed during this transmission and/or prior to the blood being provided to the extracorporeal circuit 12. As described above, replacement fluid (RP) may be added to the blood prior to or after the blood being transmitted to the extracorporeal circuit 12. Certain information about the patient, such as blood pressure, pulse, heart rate and/or the like, is transmitted or provided to the extracorporeal circuit 12 or the controller 14 therein.

Blood that exits the extracorporeal circuit 12 is transmitted or provided back to the aorta or central arterial branches, for example, of the patient 10. Certain properties of the blood, such as temperature (T), pressure (P), velocity (V), acceleration (A), number and/or type of certain blood cells (BC), heparin levels (H), plasma levels (Pl) and/or the like, are measured or analyzed during the transmission of the blood from the extracorporeal circuit 12 to the aorta or central arterial branches of the patient 10. The control or monitor board 14 employs the algorithm described above to control operation of the one or more pumps 16, to thereby pulsate the blood as it exits the extracorporeal circuit 12 and is returned to the patient. As shown in FIG. 2, various parameters or characteristics (e.g., temperature) of the blood is monitored or measured throughout its transmission through the extracorporeal circuit 12.

In some embodiments, to administer the treatment, a catheter may be placed as high as possible in the thoracic spine of the patient to obtain the neurostimulation benefit of blood supply to the spinal nervous system. Such placement is also above the renal arteries, which results in the benefit of blood supply to the renal system. Amplitude of pulsating flow is directly associated with enhanced renal flow, which results in improved organ function that will enhance body function between treatments.

Due to the complexities in understanding the physiology related to the use of apheresis to treat a wide variety of patients, the American Society for Apheresis (ASFA) has developed a system that incorporates evidence-based medicine. ASFA has created a well-defined and widely accepted categories and recommendations based on a grade system that account for the methodological quality of supporting evidence-based medicine. The disclosed therapeutic apheresis system and methods conforms with the ASFA categories and guidelines for treating patients that benefit from therapeutic apheresis.

For example, if traditional apheresis is used following cardiovascular injury, limited native pulsatile cardiac function of the damaged heart is improved due to a decrease of immediate damage by immune complexes to heart tissue. The disclosed therapeutic apheresis system would affect the secondary lymphatic system to treat underlying immune causes of progression of disease that would decrease immune insult/injury to the heart, allowing remodeling of heart tissue. Also, heart failure patients with decreased ejection fraction will benefit from increased blood flow velocity that improves perfusion to the capillaries for exchange. This is achieved in this system by increasing the energy of the mass traveling down the aorta. The increased energy may be created via pump to produce changes in augmented pulsatile properties of stroke volume ejected as part of this system. These changes in the pulsed flow of blood allows for perfusion to more tissue. The change or increase in blood flow velocity in at least a portion of the blood with simultaneous plasma exchange and transvascular flux of proteins throughout the arterial system connected to the secondary lymphatic system also immunomodulates the underlying cardiovascular disease process.

With regards to hemodynamics and fluid shifts, mortality and morbidity of heart failure is not improved by diuretics. Diuretics were found to reduce symptomatic heart failure such as dyspnea and only for this reason decreased re-hospitalization only in early heart failure states. With regards to treatment of heart failure, it was found that increased use of diuretics affected resistance. Resistance to diuretics indicated worsening heart failure. Long-term diuretic use leads to increased mortality.

Studies show that treating with digoxin instead of diuretics in heart failure states reduces all-cause mortality and all-cause hospitalizations in heart failure. Digoxin is used in the treatment of arrhythmias such as those that lead to insufficient diastolic filling times. Digoxin leads to improved pump function of the diseased heart specifically by delivering an overall improved pulsed blood flow.

In an already compromised cardiovascular system, such as when heart failure occurs, increase in fluid shifts without the use of diuretics do not cause disease to worsen. Hence, fluid shifts do not affect overall pressures in the body. This suggests that improvement of flow dynamics with regards to the pulsation of blood flow improves diseased cardiovascular state, and thus the disclosed therapeutic apheresis methods offer significant promise in the treatment of cardiovascular disease.

Notwithstanding that any numerical ranges and parameters setting forth the broad scope of the disclosure are approximations, the numerical values set forth in the specific examples are reported as precisely as possible. Any numerical value, however, inherently contain certain errors necessarily resulting from the standard deviation found in their respective testing measurements.

The system and/or apparatus disclosed herein may be stand-alone or operate separate and distinct from any other medical or healthcare system or apparatus. Alternatively, the system and/or apparatus disclosed herein may work in conjunction with one or more of hemodialysis, cardiopulmonary bypass, extracorporeal membrane oxygenation (ECMO), and/or aquapheresis.

Therefore, the present disclosure allows attainment of the ends and advantages mentioned as well as those that are inherent therein.

The previous description of the disclosed embodiments is provided to enable any person skilled in the art to make or use the invention disclosed herein. Various modifications to these embodiments will be readily apparent to those skilled in the art, and the generic principles defined herein may be applied to other embodiments without departing from the spirit or scope of the disclosure. Thus, the present disclosure is not intended to be limited to the embodiments shown herein but is to be accorded the widest scope consistent with the principles and novel features disclosed herein.

All references cited herein are expressly incorporated by reference.

What is claimed is:

1. A method of performing therapeutic apheresis on a patient that has a heart that generates a pulse, an arterial system, blood within the arterial system having a pulse velocity defined as the velocity of the blood when the pulse is at peak amplitude, and a secondary lymphoid system, the method comprising the steps of:
   a. introducing arterial blood having a first pulse velocity from the patient into an extracorporeal circuit;
   b. performing apheresis on the blood to remove one or more components from the blood; and
   c. returning a portion of the blood from the extracorporeal circuit to the arterial of the patient in pulsatile flow at a second pulse velocity that is different from the first pulse velocity;
   wherein combining apheresis and return of a portion of the blood in pulsatile flow causes a migration of immune factors from the secondary lymphoid system to an intravascular space for removal.

2. The method of claim 1, wherein the extracorporeal circuit comprises one or more of an automated blood cell separator, a pump, a sensor, and a heat exchanger.

3. The method of claim 1, wherein one or more pumps create the pulsatile flow.

4. The method of claim 1, wherein the pulsatile flow is created by a pulse wave from the patient.

5. The method of claim 1, wherein the portion of the blood further includes a replacement fluid.

6. The method of claim 5, wherein the replacement fluid includes a therapeutic agent.

7. The method of claim 1, wherein the pulsatile flow coincides with the onset of ventricular systole.

8. The method of claim 2, wherein the pulsatile flow is initiated by ejection from the one or more pumps and coincides with the onset of ventricular systole.

9. The method of claim 2, wherein the pump is filled from a distal systemic artery and returns volume to a proximal systemic artery.

10. The method of claim 1, wherein the second velocity is higher than the first velocity.

11. The method of claim 1, wherein the second velocity is lower than the first velocity.

12. The method of claim 2, wherein the second velocity is higher than the first velocity.

13. The method of claim 2, wherein the second velocity is lower than the first velocity.

14. The method of claim 3, wherein the second velocity is higher than the first velocity.

15. The method of claim 3, wherein the second velocity is lower than the first velocity.

16. The method of claim 5, wherein the second velocity is higher than the first velocity.

17. The method of claim 5, wherein the second velocity is lower than the first velocity.

18. The method of claim 6, wherein the second velocity is higher than the first velocity.

19. The method of claim 6, wherein the second velocity is lower than the first velocity.

* * * * *